United States Patent
Pflum

(10) Patent No.: US 10,143,560 B2
(45) Date of Patent: Dec. 4, 2018

(54) SAC FOR USE IN SPINAL SURGERY

(71) Applicant: Francis Pflum, Middletown, NJ (US)

(72) Inventor: Francis Pflum, Middletown, NJ (US)

(*) Notice: Subject to any disclaimer, the term of this patent is extended or adjusted under 35 U.S.C. 154(b) by 0 days.

(21) Appl. No.: 14/708,082

(22) Filed: May 8, 2015

(65) Prior Publication Data

US 2015/0238321 A1 Aug. 27, 2015

Related U.S. Application Data

(63) Continuation-in-part of application No. 13/507,725, filed on Jul. 23, 2012, now abandoned, which is a
(Continued)

(51) Int. Cl.
 A61F 2/44 (2006.01)
 A61F 2/28 (2006.01)
 A61F 2/30 (2006.01)

(52) U.S. Cl.
 CPC .............. *A61F 2/441* (2013.01); *A61F 2/442* (2013.01); *A61F 2/28* (2013.01); *A61F 2/4455* (2013.01); *A61F 2002/2835* (2013.01); *A61F 2002/30011* (2013.01); *A61F 2002/30032* (2013.01); *A61F 2002/30062* (2013.01); *A61F 2002/30075* (2013.01); *A61F 2002/30253* (2013.01); *A61F 2002/30565* (2013.01); *A61F 2002/30583* (2013.01); *A61F 2002/4495* (2013.01);
(Continued)

(58) Field of Classification Search
 CPC .... A61F 2002/30013; A61F 2250/0024; A61F 2/441
 See application file for complete search history.

(56) References Cited

U.S. PATENT DOCUMENTS 4,349,921 A 9/1982 Kuntz
5,397,364 A 3/1995 Kozak et al.
(Continued)

FOREIGN PATENT DOCUMENTS

WO WO 1995/031948 11/1995
WO WO 2003/007853 1/2003
(Continued)

OTHER PUBLICATIONS

Halverson et al. Foreigh bodies: radiopaque compared to what? Pediatric Radiology, vol. 43, Issue 9, pp. 1103-1107. Sep. 2013.*
(Continued)

*Primary Examiner* — David Bates
(74) *Attorney, Agent, or Firm* — White & Case LLP

(57) ABSTRACT

A method for fusing spinal bone is provided. The method comprises placing a sac between two or more adjacent sections of the spine to be fused, inserting a cage into the sac, and filling the sac with bone tissue. The surfaces of the sac abutting the sections of the spine comprise porous material for allowing bone to grow between the spine and the sac. Surfaces of the sac not abutting the sections of the spine are nonporous to bodily fluids and thereby prevent premature deterioration of the bone tissue inside the sac. The cage maintains the sac in an expanded state upon filling. A kit comprising the sac and cage is also provided. In other embodiments of the invention, the method comprises placing an inner sac inside the inventive sac and filling the sacs with bone tissue for fusion of spinal bone.

14 Claims, 3 Drawing Sheets

Related U.S. Application Data continuation of application No. 11/450,600, filed on Jun. 8, 2006, now Pat. No. 8,226,722.

(52) U.S. Cl.
CPC ............... *A61F 2210/0004* (2013.01); *A61F 2210/0061* (2013.01); *A61F 2210/0085* (2013.01); *A61F 2230/0076* (2013.01); *A61F 2250/0003* (2013.01); *A61F 2250/003* (2013.01); *A61F 2250/0023* (2013.01); *A61F 2310/00353* (2013.01)

(56) References Cited

U.S. PATENT DOCUMENTS

| | | | |
|---|---|---|---|
| 5,514,180 | A | 5/1996 | Heggeness et al. |
| 5,549,679 | A * | 8/1996 | Kuslich ............... A61F 2/0063 606/247 |
| 5,571,189 | A | 11/1996 | Kuslich ............... 623/17.12 |
| 5,609,635 | A | 3/1997 | Michelson |
| 5,645,598 | A | 7/1997 | Brosnahan, III |
| 5,700,291 | A | 12/1997 | Kuslich et al. |
| 5,702,449 | A | 12/1997 | McKay |
| 5,888,223 | A | 3/1999 | Bray, Jr. |
| 6,241,770 | B1 | 6/2001 | Michelson |
| 6,332,894 | B1 | 12/2001 | Stalcup et al. |
| 6,419,704 | B1 | 7/2002 | Ferree |
| 6,582,467 | B1 | 6/2003 | Teitelbaum et al. |
| 6,632,235 | B2 | 10/2003 | Weikel et al. |
| 6,800,245 | B1 | 10/2004 | Erbe et al. |
| 6,835,206 | B2 | 12/2004 | Jackson |
| 6,958,077 | B2 | 10/2005 | Suddaby |
| 6,969,405 | B2 | 11/2005 | Suddaby |
| 7,001,431 | B2 | 2/2006 | Bao et al. |
| 7,220,282 | B2 | 5/2007 | Kuslich |
| 7,226,481 | B2 | 6/2007 | Kuslich |
| 7,351,244 | B2 | 4/2008 | Hamada |
| 7,399,739 | B2 | 7/2008 | Shimp |
| 8,906,094 | B2 | 12/2014 | Roche et al. |
| 2002/0068974 | A1 | 6/2002 | Kuslich et al. |
| 2002/0123750 | A1 | 9/2002 | Eisermann et al. ............ 606/69 |
| 2003/0069641 | A1 | 4/2003 | Reuter et al. |
| 2004/0073308 | A1 | 4/2004 | Kuslich et al. |
| 2004/0091462 | A1 | 5/2004 | Lin et al. |
| 2004/0230309 | A1 | 11/2004 | DiMauro et al. |
| 2004/0267368 | A1 | 12/2004 | Kuslich |
| 2005/0043798 | A1 | 2/2005 | Eckman |
| 2005/0055094 | A1 | 3/2005 | Kuslich |
| 2005/0216089 | A1 | 9/2005 | Michelson |
| 2006/0293749 | A1 | 12/2006 | Hudgins et al. |
| 2007/0093822 | A1 | 4/2007 | DuToit et al. |
| 2007/0168031 | A1 | 7/2007 | Hudgins et al. |
| 2007/0270950 | A1 | 11/2007 | Trieu |
| 2007/0276491 | A1 * | 11/2007 | Ahrens ............... A61F 2/441 623/17.11 |
| 2008/0086133 | A1 | 4/2008 | Kuslich et al. |

FOREIGN PATENT DOCUMENTS

| | | |
|---|---|---|
| WO | WO 2004/041075 | 5/2004 |
| WO | WO-2007/146738 | 12/2007 |
| WO | WO 2008/008522 | 1/2008 |
| WO | WO 2008/063642 | 5/2008 |

OTHER PUBLICATIONS

International Search Report and Written Opinion for PCT/US2007/070602.
International Preliminary Examination Report for PCT/US2007/070602.
Future of Spine Surgery "Beyond Total Disc", Replication Medical, Inc. Neudisc, Viscogliosi Bros., LLC, 2004.
Pflum et al., "Arthroscopic Anterior Diskectomy of the Cervical Spine", Arthroscopy: The J. of Arthroscopic and Related Surgery, vol. 24, No. 5 (May 2008): pp. 612-614.
CusMed-PawTex—Spine Implant Product Listing, retrieved from www.cusmed.com/spineimplants.html on May 27, 2015.
RISE Product Information, from Globus Medical, retrieved from www.globusmedical.com/portfolio/rise/ on May 27, 2015.
Opticage-PerX360° System—Product Information, from Interventional Spine, retrieved from www.i-spineinc.com on May 27, 2015.
Precision Spine Product Listing, retrieved from www.precisionspineinc.com/4019_products.html on May 27, 2015.
SpineNet Product Listing, retrieved from www.spinenetllc.com/products/ on May 27, 2015.
OpiMesh Product Information, from Spineology, retrieved from www.spineology.com/fb/us/products_us/optimesh.html on May 27, 2015.
SUSTAIN and SUSTAIN-R, Large, from Globus Medical, retrieved from www.globusmedical.com/portfolio/sustain-sustain-r-large/ on May 27, 2015.
Titan Spine Product Line, retrieved from www.titanspine.com/content/products/overview.htm on May 27, 2015.

* cited by examiner

SAC FOR USE IN SPINAL SURGERY

This application is a continuation-in-part of U.S. patent application Ser. No. 13/507,725, filed on Jul. 23, 2012, which is a continuation of U.S. patent application Ser. No. 11/450,600, filed on Jun. 8, 2006, now U.S. Pat. No. 8,226,722. The contents of each of these prior applications is incorporated by reference herein in its entirety.

FIELD OF THE INVENTION

The present invention is directed to the field of medical technology. More specifically, the present invention is directed to methods for reconstructing sections of the spine using an implantable sac containing bone tissue and/or other structural material.

BACKGROUND OF THE INVENTION

Certain technological advances have recently been applied to previously-accepted medical treatments of maladies of the spine. These technological advances have significantly facilitated the treatment of these spinal difficulties.

Specifically, these new treatments involve the use of scopes or cannulas placed into the spine and small porous bags filled with bone chips to treat fractures of the spine and to fuse individual bone segments of the spine together. These bags are porous to allow ingrowth from adjacent bone and thereby join the bone segments.

There are certain problems with these prior art bags of bone chips for treating spinal maladies. If the bag is placed in the disc space, the exposed pores on the sides of the bag may allow the passage of body fluids through the pores into the bag. These bodily fluids have the opportunity to digest, soften, and change the non-compressive strength of the bag, thereby causing premature collapse before bone fusion has completed.

There are also uncertainties regarding an optimum size of the bag to be used. For example, if a surgeon wishes to place the bag in the disc space, there are uncertainties regarding the desired size, shape, and height of the bag.

Finally, there are issues regarding optimum orientation of the bag in the area to be fused, and assessment of proper orientation in position.

U.S. Pat. No. 5,571,189 discloses an expandable, porous fabric implant or bag for insertion into the interior of a reamed out disc which is packed with material to stabilize the spinal segment. The fabric pores allow for tissue ingrowth through the implant. A drawback to this bag is that bodily fluids can enter the porous sides of the bag and thereby digest or partially digest inserted bone graft material before fusion has completed, and thereby potentially causing failure of the implant or graft.

SUMMARY OF THE INVENTION

The present invention addresses the above problems regarding the use of implantable bags for spinal fusion. An object of the invention is to facilitate the use, effectiveness, and safety of a sac comprising bone tissue and/or other structural material which is implanted into a section of the spine of a patient.

A first aspect of the present invention provides for a method for fusing spinal bone. The method comprises placing a sac between two or more adjacent sections of the spine to be fused, and filling the sac with bone tissue. The surfaces of the sac abutting the sections of the spine comprise porous material for allowing bone to grow between the spine and the sac. Surfaces of the sac not abutting the sections of the spine are nonporous to bodily fluids and thereby prevent premature deterioration of the bone tissue inside the sac. A porous sac material is to be considered as a substance that allows bone to grow through it. A non-porous sac material is to be considered as a substance that prevents a significant amount of bodily fluids from passing through and dissolving or deteriorating the bone fragments contained inside the sac. The sac is free of structural walls affixed to the peripheral surfaces of the sac.

Another aspect of the invention provides for a sac for fusing spinal bone. The sac has generally flat upper and lower surfaces and a peripheral surface between the upper and lower surfaces. The surfaces of the sac define an interior volume intended to be filled with bone tissue and/or other structural material prior to placement in the spine. The upper and lower surfaces of the sac comprise porous material for allowing bone to grow between the spine and the sac, and the peripheral surface is nonporous to bodily fluids to prevent deterioration of the bone tissue inside the sac. The sac is free of structural walls affixed to the peripheral surfaces of the sac.

Another aspect of the invention provides for a kit for fusing spinal bone. The kit comprises the sac according to an aspect of the invention; and an apparatus for filling the sac. The sac is filled with bone tissue and implanted into a section of a patient's spine.

Further aspects of the invention involve the use of a cage to maintain the inventive sac in an expanded state after implantation in the body. The term "cage" is to be understood as any prosthetic device which can be placed in the interior of the inventive sac for the purpose of maintaining the sac in an expanded state upon filling to assist during spinal fusion. Examples of cages include fusion cages and intervertebral cages which are inserted into the previously-described inventive sac.

In this regard, an aspect of the invention provides for a method for fusing spinal bone involving the inventive sac and a cage. The method comprises the steps of: providing the inventive sac; delivering the sac in a collapsed state to the area of implantation in the spine; and inserting a cage in the interior of the sac, the cage structurally configured to maintain the sac in an expanded state upon filling. In a further embodiment, the inventive method comprises filling the sac containing the cage with bone tissue.

The sequence of steps of the inventive method can be altered as may be deemed appropriate by the surgeon. For example, the cage can be inserted into the sac after the sac has been delivered to the area of implantation, or the cage can be inserted into the sac prior to delivery of the sac and cage to the area of implantation.

In one embodiment of the invention, the sac has a unitary structure and generally flat upper and lower surfaces and a peripheral surface between the upper and lower surfaces. The surfaces of the sac define an interior volume to be filled with the cage and any bone tissue without leakage of the sac contents when filled. The upper and lower surfaces of the sac comprise porous material and the peripheral surface is nonporous to bodily fluids. The porous material allows for bone to grow into and out of the upper and lower surfaces of the sac. The sac is free of structural walls affixed to the peripheral surface.

Another aspect of the invention provides for a kit for fusing spinal bone containing the inventive sac and a cage. The kit comprises the inventive sac for fusing spinal bone;

a cage which is structurally configured to fit inside the sac after expansion and to maintain the sac in an expanded state upon filling; and optionally a device for filling the sac.

In one embodiment, the sac has a unitary structure and generally flat upper and lower surfaces and a peripheral surface between the upper and lower surfaces. The sac has a closed collapsible state for delivery to an implantation location, wherein the sac is folded upon itself, and an opened expanded state when positioned at the implantation location. The surfaces of the sac define an interior volume to be filled with the cage and any bone tissue without leakage of sac contents when filled. The upper and lower surfaces of the sac comprise porous material for allowing bone to grow into and out of the interior volume when the sac is in the expanded state, and the peripheral surface of the sac is nonporous for preventing bodily fluids from entering the sac when the sac is in the expanded state. The sac is free of structural walls affixed to the peripheral surface, and the sac is pre-sized and pre-shaped to fit complimentary within the implantation location.

Any of the disclosed embodiments of the sac can be used in conjunction with any of the methods or kits provided by the various aspects of the invention.

Another aspect of the invention is directed to a method for fusing spinal bone comprising the inventive sac (termed an outer sac in this aspect of the invention) in conjunction with an inner sac which serves to enclose bone tissue. The method comprises providing a collapsible outer sac having a unitary structure and generally flat upper and lower surfaces and a peripheral surface between the upper and lower surfaces; delivering the outer sac in a collapsed state to the area of implantation in the spine; inserting an inner sac in the interior of the outer sac; and filling the inner sac and outer sac to an expanded state with bone tissue.

In an embodiment of this aspect of the invention, the inner sac is structurally configured to maintain the outer sac in an expanded state upon filling. There may also be a plurality of inner sacs of the same or different sizes to contain particular quantities of bone tissue to promote spinal fusion.

DETAILED DESCRIPTION

I. Sac

Figure 1:
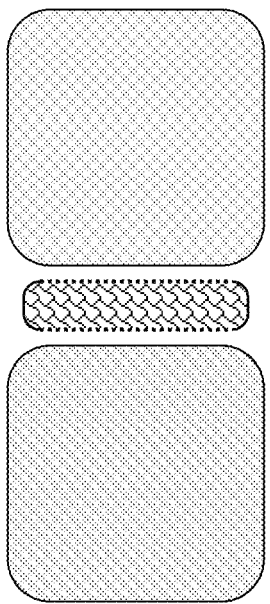
FIG. 1 is a cross-sectional view of a sac according to an embodiment of the present invention which has been implanted between two sections of the spine.

The present invention may be used to fuse any sections of the spine, such as vertebra or sections of vertebra. These sections of the spine can be located at any part of the spine, such as the lumbar spine, the cervical spine, or the thoracic spine. The invention can also be used to fuse adjacent regions of the spine. In one embodiment, the invention can be used to fuse sections of the cervical spine. For patients with severe degenerative illnesses, the method can be used to treat multiple sections of the spine and thereby provide a measure of relief to the patient.

The sac will normally be implanted in the spine during a surgical procedure, such as during an arthroscopic or endoscopic procedure. Arthroscopic surgery is a minimally invasive surgical procedure in which a physical examination of the interior of a joint is performed using an arthroscope, a type of endoscope that is inserted into the joint through a small incision.

In contrast to traditional surgery in which the joint has to be opened up fully, endoscopic surgery generally requires only small incisions for the endoscope and for the surgical instruments. In certain surgical procedures, a single incision can be used for both the endoscope and the surgical instruments. This procedure reduces the recovery time of the patient and may increase the rate of surgical success due to reduced trauma to the connective tissue.

In the cervical spine, if fusion is desired, the standard of care is to harvest a bone graft from the patient, and to replace a damaged or deteriorating disc with the harvested bone. The present invention can be used to increase the height of the segments and the discs and disc space of the spine, when such a procedure is desirable. The invention can also be used to support or rework or enlarge the neural foramina, openings between every two vertebrae where the nerve roots exit the spine to reach the rest of the body. The procedure allows for opening a window to replace or fuse segments of the spine in need of repair, and fusion of the segments containing the bone graft.

The peripheral sides of the sac have a height which is generally equal to the desired height or distance between the vertebra and bones to be fused. The surfaces of the sac define an interior volume which is intended to be filled with bone tissue or other substances before or during implantation in the spine of a patient.

The term "bone tissue" is meant to comprise bone chips, bone fragments, osteocytes, bone cement, cartilage chips, cartilage-forming material, or any other type of natural, bioengineered, or synthetic bone tissue, and combinations thereof. The bone tissue may also comprise expandable bone graft material such as compressed demineralized cancellous bone which absorbs fluid and expands inside the novel sac at the implantation site. The bone tissue regenerates or facilitates regeneration of natural bone and the fusion of the sections of the spine. The bone tissue may also be one or more sections of bone extracted from another part of the body and which approximate the size of the sac. The bone tissue may be a single unitary element, or it may comprise a plurality of separate elements of the same or different composition which will be implanted in the body. The bone tissue will normally comprise living bone tissue to facilitate the fusion of the sections of the spine, although the use of non-living bone tissue is within the scope of the present invention. Biocompatible glue may be used to bond the portions of the bone tissue to form a larger structure inside the sac. An injectable bone graft replacement may also be used to facilitate bone growth and spinal fusion.

In addition to or in place of bone tissue, the sac may comprise elements which are biocompatible and which support or foster the growth of bone in or into the sac. For example, the sac may comprise an inorganic bone growth support substance which is any substance which supports or assists the growth of bone tissue in or into the implant area. The bone growth support may comprise a filler material to reduce the amount of bone tissue required to fill the sac. In one embodiment of the invention, the bone growth support is calcium phosphate or hydroxyapatite. Such inert fillers are known in the art.

The sac may also further comprise a hydrogel, or a hydrogel-type substance, in addition to or in place of bone tissue. Hydrogels generally are cross-linked polymers which hydrate to absorb water and form solids having physical properties similar to those of gelatin or soft contact lenses. A sac containing such substance is usually nonporous on all surfaces is placed into the nuclear cavity of the disc and hydrates to expand and fill the cavity. In alternative embodiments, the sac may be slightly porous. The hydrogel is compressible and by this means, allows motion, much like a normal disc nucleus. The hydrogel may be in a hydrated condition or in an unhydrated condition when it is placed in the sac for implantation. Placement of a hydrogel implant within the disc space generally provides the lift that is necessary to restore and maintain disc space height in most patients.

In certain embodiments, a surgeon may choose to implant a sac according to the present invention which comprises a hydrogel and which does not contain bone tissue. In such an embodiment, the hydrogel may be hydrated before it is placed into the sac.

The sequence of the steps of the method is not critical, although it will depend upon the particular medical situation. For example, the sac may be placed in position between the sections of the spine to be fused, and then filled with bone tissue (or other substances). Alternatively, the sac may be first filled outside the desired area of implantation and then placed between the sections of the spine. In another embodiment, the sac may be partly filled, moved into position, and then filled with the bone tissue. The sac does not necessarily need to be completely filled with bone tissue or other structural material. In such instances, the sac will normally be drawn around its interior contents and then closed and tightly sealed to obtain a non-leaking package.

The sac may be composed of a bio-resorbable or a non-bioresorbable material. When the sac is bio-resorbable, the sac is slowly biodegraded as bone tissue is regenerating in the area of implantation. Nevertheless, the sac has sufficient stability to maintain its shape without undergoing deterioration before fusion of the bone has been completed or before permanent stability has been obtained. If the sac is non-bio-resorbable, the sac generally remains in its original condition for an extended period of time after implantation, for example, for a year. Portions of the sac may also be bio-resorbable and other portions may be non-bio-resorbable. For example, the porous portions of the sac abutting bone may be bio-resorbable and the peripheral surfaces not abutting bone may be non-bio-resorbable.

The choice of sac size will depend upon individual circumstances and on each patient's particular anatomy, and different patients will generally require sacs of different sizes. The sac will generally be larger when a larger section of the spine must be fused, and smaller when smaller sections are to be fused. The decision to use a sac having a particular size can be can be made in advance if the surgeon is aware of the patient's particular needs. Alternatively, the decision of a particularly-sized sac can be made intraoperatively using measurements obtained during the surgery. In one embodiment, the sac has a diameter of about 12 mm, and a height of about 6-7 mm.

For example, prior to insertion of the sac, a guidewire or cannula of known length may be doubled over on top of itself and the double end inserted into a delivery tube into the area of the spine to be fused. The spinal area can be monitored using medical imaging. With knowledge of the length and width of the delivery tube, the length of the guidewire in the patient, and the appearance of the wire under imaging, the appropriate size for the circumference of the sac can be determined.

The shape of the sac will be chosen so as to fit in its intended area of implantation. In general, the surfaces of the sac and the existing bone will generally be flat in order to maximize apposition or contact between the surfaces. If the surfaces of the spine are not flat, these surfaces may be shaved or planed so as to make them planar prior to implantation, and to encourage growth and ingrowth of bone into the implant area. Alternatively, a surgeon may select a sac which has non-flat surfaces which complement or mate with the existing bone surfaces. The surfaces of the sac which contact bone are porous to permit bone ingrowth and fusion, and the surfaces of the sac not contacting bone are non-porous. The sac is also pre-sized and pre-shaped to fit complementary within the implantation location.

In one embodiment, the sac has the general appearance of a pill. In such an embodiment, the sac has flat top and bottom surfaces, and a peripheral surface between the upper and lower surfaces. The upper and lower surfaces of the sac may have a generally non-rectilinear, round, or oblate shape. In general, sharp vertices or points will be avoided to prevent pain or damage to existing bone. In general, the sac will have an overall round or oval shape, although any shape can be used as determined by the surgeon.

The entire top and bottom surfaces of the sac do not necessarily have to be porous, and there can be portions of these surfaces which are non-porous. For example, if the diameter of the sac is larger than the adjoining bone, a central portion of the sac which will contact bone may be porous, and the rim portion of the sac which would not contact bone may be non-porous.

The sac may be formed from natural materials, synthetic materials, or a combination of both. Examples of materials of construction include metals such as titanium or tantalum, and polymers such as high density polyethylene and polyurethane. It will be obvious that the material chosen must be biocompatible to avoid rejection by the body, and such materials are known to those in the art.

The material chosen for the sac may be a woven or non-woven substance such as a fabric. For example, the sac may have porous woven upper and lower surfaces which are intended to abut existing bone, and a non-porous non-woven peripheral surface which would not abut bone tissue. The sac may also be formed from a unitary sheet of a material in which pores, holes or perforations have been made in the areas which are to abut bone in the spine. These perforations may be made using a punch or other such device. The sac may also be formed of two or more materials, such as a synthetic polymer interwoven with metallic threads or fibers.

The sac has an opening through which the bone tissue can be placed using any convenient means, such as a syringe, cannula, forceps, or other convenient means. The sac can be closed after filling using any convenient means, such as clips, sutures, staples, heat sealing, snares, or other techniques known in the art.

The sac can be delivered to the area of implantation via a cannula, endoscope, or arthroscope, or using other delivery means. Cannulas and arthroscopes generally have a fairly narrow diameter in order to minimize tissue damage. For example, a cannula used for spinal surgery may have a diameter of about 8 mm. In order to fit the sac through a cannula or other narrow delivery tube, the sac may be collapsible or have a spring mechanism so that it can be folded upon itself prior to insertion. The scopes, cannulas, or other delivery means can deliver the sac to the spine at any position along the disc, for example, anteriorly, posteriorly, extreme laterally, posterolaterally, or via a transforaminal approach.

After delivery to the appropriate location in the body, the spring mechanism can be activated to expand the sac to its full shape for final installation/implantation and filling. The sac can be filled with its contents through the cannula or arthroscope, or using other means.

The sac may optionally comprise a rigid structural element for maintaining the sac in an expanded state upon filling. This structural element may be a band or wire which encircles the peripheral surface of the sac or runs circumferentially through the sac. The structural element may be present in the sac prior to implantation in the body, for example, incorporated into the sac during its manufacture, or the structural element may be placed in the sac during the procedure.

The structural element is generally very flexible to permit facile insertion and movement during installation in the sac. The structural element may be placed in the sac via a delivery tube during the implantation procedure, or it may be already located in the sac prior to implantation. When the sac with the structural element is placed through the delivery tube, it may open in a predetermined manner so as to orient the sac in the proper position prior to insertion of bone tissue.

The structural element can be manufactured from any type of material, such as plastic or metal. The structural element may be pre-stressed so as to have a resiliency or memory effect to facilitate its proper placement in the sac or to expand the sac into the correct position or shape.

The rigid structural element may be opaque to medical imaging equipment. In such a manner, a surgeon implanting the sac in the spine can monitor the placement of the sac relative to existing bone or tissues using imaging techniques and thereby facilitate implantation. A non-exhaustive list of medical imaging techniques includes fluoroscopy, tomography, CAT scanning, magnetic resonance imaging, and ultrasound techniques.

The height of the sac generally corresponds to the distance between the sections of the spine to be fused in order to provide for maximal growth of bone. Alternatively, the height of the sac may be slightly or substantially larger than the distance between the sections of the spine so that the sections of the spine are moved apart, e.g. to lengthen or straighten the spine.

A radio-opaque wire or other structural element may be incorporated into the equator or other part of the sac for documentation of placement for safety reasons or to monitor the occurrence of any migration of the sac which may occur.

II. Sac and Cage

The invention has been discussed above with respect to the novel sac, a kit comprising the sac, and to methods of using the sac for fusing spinal bone. These aspects of the invention provide significant advances in the field of spinal surgery and spinal fusion.

Further aspects of the invention provide methods of using the sac in combination with a cage which is structurally configured to maintain the sac in an expanded state upon filling; and kits comprising (a) the inventive sac, (b) a cage which is structurally configured to fit inside the sac after expansion and to maintain the sac in an expanded state upon filling, and (c) optionally a device for filling the sac. These aspects of the invention will now be discussed.

An aspect of the invention provides a method for fusing spinal bone using the inventive sac in combination with a cage. The method comprises the steps of: providing the inventive sac; delivering the sac in a collapsed state to the area of implantation in the spine; and inserting a cage in the interior of the sac, the cage structurally configured to maintain the sac in an expanded state upon filling. In a further embodiment, the method may involve filling the sac around the cage to an expanded state with bone tissue. This step of filling the sac may include placing bone tissue inside the cage if the cage has a fillable interior.

The sequence of steps of the inventive method can be altered as may be deemed appropriate by the surgeon. For example, the cage can be inserted into the sac in a collapsed state after the sac has been delivered to the area of implantation, or the cage can be first inserted in the sac and then the sac and cage can be together delivered in a collapsed state to the area of implantation and then expanded. If the sac is to be filled with bone tissue in addition to the cage, the bone tissue can be added after the sac and cage are at the area of implantation and expanded, or the sac can be filled with bone tissue prior to delivery. The sac can also be partly filled prior to delivery to the intended area of implantation, and then filled completely after the sac and cage have been delivered. In such embodiments, the bone tissue would be inserted into the sac around the cage. The sac is structurally configured to prevent leakage of the sac contents after filling.

The method can be used to fuse sections of the spine, such as sections of the lumbar spine, the cervical spine, or the thoracic spine, or the invention can be used to fuse adjacent parts of the spine. The inventive method can be performed during an endoscopic or arthroscopic surgery procedure, or via cannula as deemed appropriate by the surgeon.

The cage can have any kind of three-dimensional shape, for example, circular, rectangular, square, or hexagonal. The cage can be purchased commercially or custom-manufactured. Examples of commercial cages suitable for use in the present invention are the RISE all-titanium expandable lumbar fusion device and the SUSTAIN Large trapezoidal thoracolumbar intervertebral fusion device, both manufactured by Globus Medical Inc. (Audubon, Pa.). Another example of a commercially-available cage is OPTICAGE (part of the PERX360° system), available from Interventional Spine (Irvine, Calif.). In one embodiment, the cage has generally flat upper and lower surfaces in the expanded state. The generally flat surfaces of the cage match, mate with, or engage the corresponding generally flat upper and lower surfaces of the sac so as to facilitate installation in the body.

In certain embodiments of the invention, the cage has a mechanism to urge the cage to expand from a collapsed state to its full shape for installation in the sac. For example, the cage may have a spring mechanism which is activated to expand the cage to its full shape for installation in the body after the cage has been positioned by the surgeon. The cage may have a mechanism which retains the sac in an expanded state after the sac has been filled. For example, the cage may have a locking mechanism to ensure that the cage remains permanently in the expanded condition in the sac after installation. In alternative embodiments of the invention, the cage may not be expandable and may have a fixed and static configuration. The choice of cage will depend upon the patient's particular anatomy and surgeon's judgment.

The cage can be formed of any material which would be suitable for implantation in the body. For example, the cage can be made of a metallic, polymeric, or ceramic material, or from a combination of such materials. The cage can also be made from a nanocomposite. The cage may also be manufactured using conventional technologies, or it can be printed using a 3D printer. It is understood that the cage will need to be made of materials which are non-toxic and biologically acceptable, and which can last in a patient's body for years or decades without developing structural weaknesses or failure. If a patient has an allergy or sensitivity to a particular material, the surgeon can select an implant prepared from alternative material prior to surgery which would provide improved biocompatibility to the patient's body. The cage can be custom-manufactured or selected from among commercially-available cages.

The cage may have a collapsed state in which the cage occupies a minimal amount space so as to facilitate insertion into the sac, and an expanded state in which the cage provides structural support for the sac. For example, in the collapsed state, the cage can have such dimensions as to fit through an arthroscopic or endoscopic incision or an incision for a cannula. In certain embodiments, the cage may have an adjustable height to facilitate installation of the cage in the sac and body. The cage may also have a predetermined height after expansion in the sac. In one embodiment, the height of the cage after expansion is generally equivalent to the height of the peripheral surface of the sac, and this height is generally equivalent to the desired height or distance between vertebra or bones to be fused. Alternatively, the height of the cage may be slightly or substantially larger than the distance between the sections of the spine so that the sections of the spine are moved apart, e.g. to lengthen or straighten the spine.

In further embodiments of the invention, the cage has a single fixed height which is not adjustable. As previously stated, the choice of a particular cage and sac combination, as well as selection of the bone tissue fill material for the sac and/or cage, will be determined by the surgeon prior to or during a surgical procedure.

When bone tissue is inserted into the cage and/or into the sac around the cage, the bone tissue can be in the form of a single unitary element such as a solid piece of a bone material; or the bone tissue can be in the form of a plurality of separate elements which have the same or different composition. For example, the bone tissue can comprise bone chips, bone fragments, osteocytes, bone cement, cartilage chips, cartilage-forming material, natural bone, bioengineered bone, synthetic bone, expandable bone graft material, or any combination of such materials. The bone tissue can optionally comprise one or more substances selected from the group consisting of a biocompatible glue, an inorganic bone growth support substance, and a filler material. The bone tissue can be directly inserted in the sac, or the bone tissue can be enclosed in a bag, mesh, sac, or other structure for containment.

The bone tissue (or any non-bone structural material or non-bone components) will generally be inserted into the sac around, into, or alongside the cage in such a manner that the bone tissue will grow in the sac and around the cage. After bone growth and ingrowth is completed, the cage will be surrounded by fused bone tissue. In other embodiments, the sac can be filled with a structural material which does not contain bone tissue in order to provide support to the spine while allowing natural bone ingrowth during healing and spinal fusion.

Another aspect of the invention provides for a kit for fusing spinal bone. The kit comprises the inventive sac for fusing spinal bone; a cage which is structurally configured to fit inside the sac after expansion and to maintain the sac in an expanded state upon filling; and optionally a device for filling the sac. This device for filling the sac may have any form which can transfer or transport bone tissue to the interior of the sac. In one embodiment, the device for filling the sac is a syringe or cannula which is known in the art. The filling device may be disposable or reusable.

The kit may be provided as a single sealed package, or the kit may be provided as separate components in a package. The kit may be provided in a sterilized or non-sterile condition. The sterilization may be performed using steam, ethylene oxide, radiation, or other convenient techniques known in the art.

III. Outer Sac and Inner Sac

The invention has been discussed above with respect to the novel sac, and the use of the sac in combination with an intervertebral cage. These aspects of the invention provide significant advances in the field of spinal surgery and spinal fusion.

Further aspects of the present invention are directed to methods for fusing spinal bone involve the use of a second sac inside the inventive sac. For ease of discussion, in these aspects of the invention, the inventive sac will be termed an outer sac and the second sac will be termed an inner sac. In order to promote spinal fusion, bone tissue is inserted into the inner and/or outer sacs. The outer sac will have the inventive structure previously described. In general, the features of the inventive sac (outer sac) discussed above will be equally applicable to the inner sac. For example, the descriptions of the materials of construction, delivery into the body, and collapsed and expanded states of the inventive (outer) sac will also be applicable to the inner sac.

As only the outer sac will be in contact with a patient's spine, the structure of the inner sac is not critical as it will be contained inside the outer sac. The inner sac can have any structure which will contain bone tissue for promoting spinal fusion. Generally, the inner sac will contain holes, pores, or other interstices to promote bone growth and ingrowth into the interior of the sacs so that spinal fusion is successfully accomplished. The inner sac can be in the form of a bag, mesh, pouch, sac, or other structure. There may also be a plurality of inner sacs inside the outer sac, each inner sac having the same or different structure. A non-limiting example of a suitable commercially-available mesh pouch for use as an inner sac is OptiMesh® (Spineology, St. Paul, Minn.).

The material chosen for the inner sac may be a woven or non-woven substance such as a fabric or mesh. The inner sac may also be formed from a unitary sheet of a material in which pores, holes or perforations have been made as desired, for example by using a punch or similar mechanism. The inner sac may also be formed of two or more materials, such as a synthetic polymer interwoven with metallic threads or fibers. As the inner sac is contained by the outer sac, the inner sac may have any kind of surface properties as long as it provides for bone tissue growth and ingrowth into and out of the inner and outer sacs to enable spinal fusion to take place. The inner sac can also be pre-sized and pre-shaped to fit within the our sac complementary within the implantation location.

The inner sac is contained by the outer sac which has porous upper and lower surfaces and a non-porous peripheral surface. Consequently, there is no restriction on the size of the inner sac, although it will be clear that the inner sac must be sized to fit inside the outer sac when both are fully expanded. The inner sac may be composed of a bioresorbable or a non-bioresorbable material, or both. The inner sac may also have a structural element which is opaque to medical imaging equipment to assist in placement of the inner sac. For example, the inner sac may have a band or wire which encircles the surface of the inner sac or runs circumferentially through the inner sac, or the inner sac can be woven or prepared using metallic or radio-opaque threads to facilitate visibility during medical imaging.

The inner sac has an opening through which bone tissue can be placed using any convenient device, such as a syringe, cannula, forceps, or other convenient device. The inner sac can be closed after filling using any convenient means, such as clips, sutures, staples, heat sealing, snares, or other techniques known in the art.

The inner sac can be delivered inside the outer sac using any suitable techniques, such as via a cannula, endoscope, arthroscope, or other delivery device. For example, the inner sac can have a closed collapsed state for delivery to the outer sac, wherein the sac is folded upon itself or otherwise has a minimized installation profile, and an expanded state when fully opened inside the outer sac.

Depending upon the particular implementation of the invention, the bone tissue can be inserted in the inner sac or in both the inner and outer sacs during spinal surgery. The surgeon will determine before or during surgery as to the best placement of the bone tissue in the inner and outer sacs. After the sacs are filled, the combination of the inner and outer sacs provides structural stability to the adjacent bone and maintain the spine in a desired position for spinal fusion.

An embodiment of this aspect of the invention is directed to a kit for fusing spinal bone. The kit comprises the inner and outer sacs according to the invention, and optionally a device for filling the sacs. This device may have any form which can transfer or transport bone tissue to the interior of the sac. In one embodiment, the device for filling the sac is a syringe or cannula which is known in the art. The filling device may be disposable or reusable.

In a further embodiment of the invention, a fusion cage (as discussed above) can be used in conjunction with an inner sac. The fusion cage is placed inside the inner sac which is then filled with bone tissue. The outer sac contains both the inner sac and the fusion cage and allows IV. Discussion of Figures The present invention will now be described with reference to the Figures which illustrate the general principles of the invention. FIG. 1 illustrates a cross-sectional view of an embodiment of a sac according to the present invention. The sac has been implanted schematically between two sections of the spine to be fused. The upper and lower surfaces of the sac (depicted using a dashed line) abut the existing spinal bone and comprise porous material. The porosity allows for bone to grow between the spine and the sac. The surfaces of the sac not abutting the sections of the spine are nonporous to bodily fluids and thereby prevent deterioration of the inserted bone tissue before the bone tissue has had a chance to regenerate.

Figure 2:
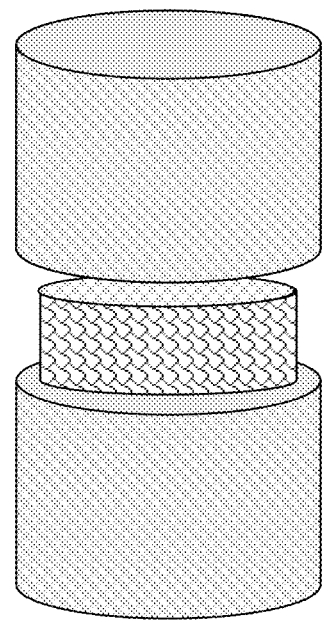
FIG. 2 is a three-dimensional perspective view of the embodiment illustrated in FIG. 1.

FIG. 2 is a three-dimensional perspective view of the embodiment illustrated in FIG. 1. FIG. 2 shows a sac according to an embodiment of the invention embedded into a portion of the spine of a patient. The surfaces of the sac abutting bone are porous and allow for bone ingrowth between the sac and the spine. The peripheral surface of the sac is non-porous to bodily fluids and thereby prevents deterioration of the bone tissue located in the sac.

For clarity of detail, FIGS. 1 and 2 show the sac as having a height which is slightly smaller than the distance between the bone to be fused. In use, the sac will nevertheless generally have the same height as the distance between the sections of the spine in order to have efficient fusion between the bone and bone tissue and to prevent inflow of bodily fluids. The height of the sac may also be larger than the distance between the sections of the spine so that the sections of the spine are moved apart during fusion.

Figure 3:
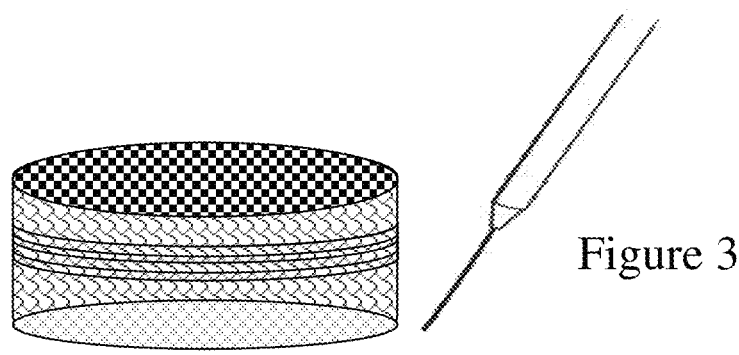
FIG. 3 illustrates a sac according to an embodiment of the present invention in the shape of a pill having a stylized spring mechanism, and a syringe for filling the sac.

FIG. 3 illustrates a sac according to an embodiment of the present invention in the shape of a pill. The sac has porous upper and lower surfaces to allow for growth of bone between the sac and the section of the spine into which the sac is implanted. The sac also has non-porous peripheral surfaces to prevent bodily fluids from entering the sac.

FIGS. 4-9 illustrate sac and cage combinations according to several exemplary embodiment of the present invention. For ease of illustration, the cages are shown in the center of the sac and away from the surfaces of the sac, although in practice, the surfaces of the sac will generally be immediately adjacent to the corresponding surfaces of the cage. Each cage has a predetermined height which is selected by the surgeon, and this height can be adjustable or it can be fixed for a particular cage. In each case, the particular height of the cage is individualized by the surgeon to each patient before or during surgery. Cages which have a variable height will typically have a collapsed state in which the cage occupies a minimum amount of space for insertion into the sac, and an expanded state in which the cage attains its desired height for supporting the patient's spine during the fusion procedure. Such cages or similar models can be purchased commercially from manufacturers such as SpineNet Inc., CusMed, PawTex, PrecisionSpine, and Titan Spine.

In each of FIGS. 4-9, the top and bottom surfaces of the sac are porous and allow bone ingrowth between the sac and the adjacent sections of the spine to be fused. The peripheral surface of the sac is non-porous to bodily fluids and thereby prevents deterioration of the inserted bone tissue before the bone tissue has had an opportunity to regenerate. Certain embodiments of the cage can be expanded from a collapsed state to an expanded state, for example, using springs or screws. For example, springs can be activated to urge the cages to expand from a collapsed state to an expanded state, and screws can be turned to move the surfaces of the cage closer or further apart. After expansion and filling, the cage maintains the sac in an expanded state while the patient's body undergoes bone fusion while recovering from the spinal fusion procedure. Consistent with the invention, particular embodiments of the cage may have only a single predetermined height and the cage is inserted into the sac without undergoing expansion.

Figure 4:
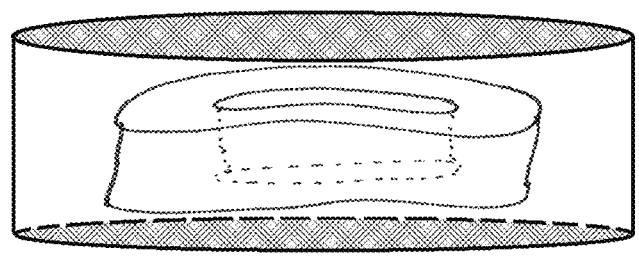
FIG. 4 illustrates a sac according to an embodiment of a further aspect of the present invention, the sac containing a cage having an opening extending vertically through the cage.

In FIG. 4, the sac contains a cage having a single large opening extending vertically through the cage. The opening is filled with bone tissue and the sac and cage are implanted into the spine with the openings of the cage facing adjacent surfaces of the spine. The sac and cage promote ingrowth of bone for spinal fusion and healing. In alternative embodiments, the cage can be provided with additional openings, for example, on the sides of the cage facing the peripheral surface of the sac, or the sac is installed with the opening facing the peripheral surface of the sac.

Figure 5:
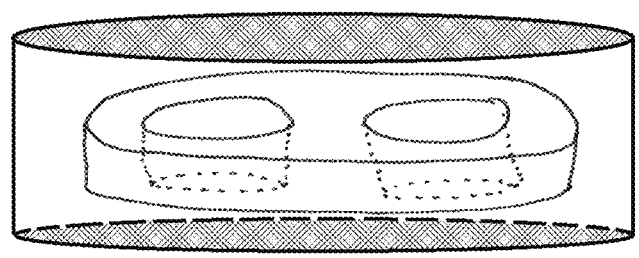
FIG. 5 illustrates an embodiment of a sac according to the invention, in which the sac contains a cage having two openings extending vertically through the cage.

FIG. 5 illustrates an alternative embodiment of a sac and cage according to the invention, in which the sac encloses a cage having two openings or bores extending vertically through the cage. These two openings can be filled with bone tissue and the sac and cage can be implanted into the patient's spine for promoting healing and spinal fusion. The cage and sac can be installed in the spine so that the openings or bores of the cage face the surfaces of the spine being fused, or the sac and cage can be installed in another orientation in accordance with the manufacturer's guidance and the surgeon's expertise.

Figure 6:
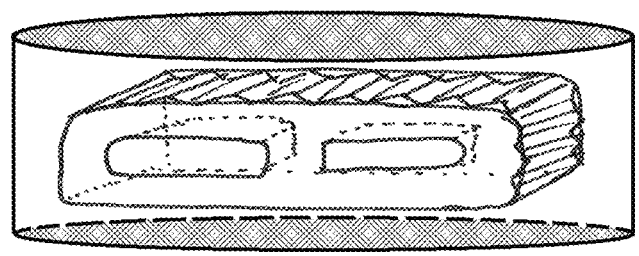
FIG. 6 illustrates a sac according to an embodiment of the invention, in which the sac contains a cage having two openings extending horizontally through the cage, and the cage has ribbing on its outer surfaces.

FIG. 6 illustrates a sac according to an embodiment of the invention, in which the sac contains a cage having two openings or bores extending horizontally through the cage, and the cage has ribbing on its outer surfaces. The ribbings provide a roughened surface to the cage, thereby assisting the cage in gripping the sac and spinal surfaces to be fused. The openings are illustrated as extending horizontally through the cage, although they may also be located vertically and extending through the ribbing. There may also be any number of openings located in any orientation. It will be evident that in any embodiment of the invention, the cage will need to be strong enough to resist any compressive forces, and that the cage also must be structurally stable so that it does not shatter or break while in the patient's body.

Figure 7:
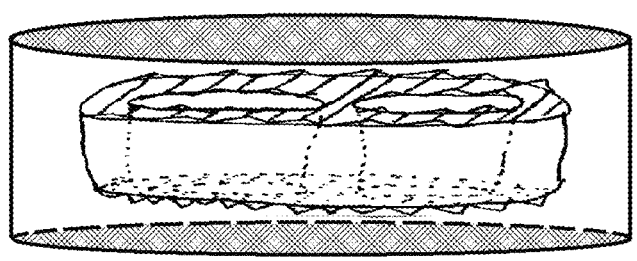
FIG. 7 illustrates a sac according to an embodiment of the invention, in which the sac contains a cage having two openings extending vertically through the cage, and the top and bottom surfaces of the cage have ribbing.

In contrast to FIG. 6 which shows a sac with a cage having bores extending horizontally through the cage, FIG. 7 illustrates a sac according to an embodiment of the invention, in which the sac contains a cage having two openings or bores extending vertically through the cage. The top and bottom surfaces of the cage in FIG. 7 have ribbing. The ribbings provide a roughened surface to the top and bottom of the cage, thereby assisting the cage in gripping the sac and spinal surfaces to be fused. The bottom of the cage has a similar or identical appearance as the top of the cage. The openings in the cage permit bone tissue to grow through the cage and sac and thereby provide a stable spinal fusion outcome for the patient. The cage can have additional openings or bores through its length.

Figure 8:
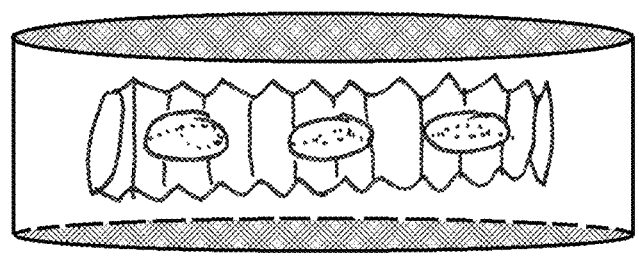
FIG. 8 illustrates a sac according to an embodiment of the invention, in which the sac contains a cylindrical cage in the general shape of a screw with threads and there are three openings which extend horizontally through the cage.

FIG. 8 illustrates a sac according to an embodiment of the invention, in which the sac contains a cylindrical cage in the general shape of a screw with threads and there are three bores holes which extend horizontally through the length of the cage. Although the bore holes are shown horizontally in the figure for clarity, the sac and cage can be installed in the patient's spine so that the bore holes of the cage are vertical. Decisions regarding installation orientation will be up to the surgeon. The threads of the surface of the cage permit the cage to grip securely into the surfaces of the sac and the surfaces of the spine which are being fused. The threads can be identical in size, height, or depth, or there may be a plurality of differently-sized threads.

Although FIGS. 4-8 illustrate the cages as having bores with run through the entire length of the cage, the cages can also have bores which do not extend throughout the entire length of the cage. In such embodiments, the bone tissue would grow into and fill the available volume of the cage. It is also within the scope of the invention that the cages have one or more bores which extend through the length of the cage and one or more bores which do not extend through the entire length of the cage, and the bores can run in any direction.

Figure 9:
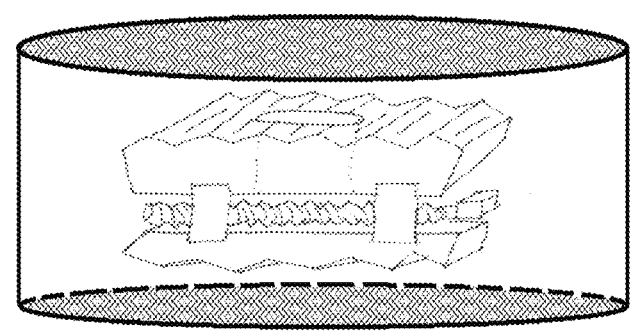
FIG. 9 illustrates a sac according to an embodiment of the invention, in which the sac contains an expandable cage having ribbing on its upper and lower surfaces, a bore through the upper and lower portions of the cage, and a screw for raising and lowering the cage between fully expanded and collapsed states.

FIG. 9 illustrates a sac according to an embodiment of the invention, in which the sac contains an expandable cage comprising upper and lower plates joined by a screw. The cage has ribbing on its upper and lower surfaces to facilitate gripping of the corresponding sac surface and adjacent portions of the spine to be fused. A bore extends through the upper and lower plates of the cage to allow bone ingrowth into the interior of the cage. The height of the cage can be adjusted by turning the screw, thereby moving the upper and lower plates closer together or further apart, that is, between collapsed and expanded states. The degree of expansion, and thus the height of the cage after expansion, will be dependent upon the patient's anatomy. A cage can have a single collapsed state and a single expanded state, or the cage can have a plurality of individual expanded states, for example, a series of discrete steps, stops, or halts which permit a limited number of configurations between the collapsed and expanded states. There may also be any number of expanded states, for example, as in the embodiment of FIG. 9, which has any degree of expansion between the collapsed state and a fully expanded state (when the cage cannot expand any further).

Figure 10:
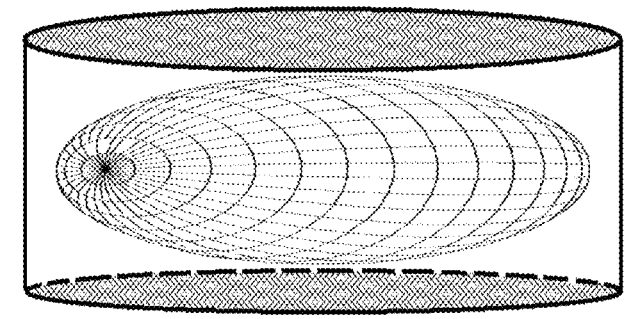
FIG. 10 illustrates a sac according to an embodiment of the invention, in which the sac (termed an outer sac in this embodiment) is used in conjunction with an inner sac which serves to enclose bone tissue.

FIG. 10 illustrates a sac according to an embodiment of the invention, in which the inventive sac (termed an outer sac in this embodiment) is used in conjunction with an inner sac which encloses bone tissue. As in the previously-discussed embodiments, the outer sac has porous upper and lower surfaces and a non-porous peripheral surface. For ease of illustration, the inner sac is shown in the center of the outer sac and away from the outer sac, although in one embodiment, the sides of the inner sac will be generally be adjacent to the outer sac and therefore conform to the shape of the outer sac. In the illustrated embodiment, the inner sac is in the form of a mesh bag which is filled with bone tissue. The inner sac can be stretchable so that its shape takes on the shape of the outer sac as the inner sac is filled with bone tissue. After the inner sac is in place and has been filled with bone tissue, the openings of the inner sac and outer sacs are sealed to prevent leakage of bone tissue.

It will be evident that other kinds of fusion cages can be effectively used in conjunction with the inventive sac. The surgeon who will be conducting the spinal fusion procedure will be able to select an appropriate cage for use with the sac. Minor variations of the disclosed procedures are also possible and will depend upon the particular embodiment of the sac and cage employed in the invention as well as the patient's anatomy and medical requirements.

While the invention has been particularly shown and described with reference to particular embodiments, those skilled in the art will understand that various changes in form and details may be made without departing from the spirit and scope of the invention.

What is claimed is:

1. A kit comprising:
   (a) a sac for fusing spinal bone, the sac having a unitary structure and generally flat upper and lower surfaces and a peripheral surface between the upper and lower surfaces, the sac having a closed collapsible state for delivery to an implantation location, wherein the sac is folded upon itself, the sac having an opened expanded state when positioned at the implantation location, wherein the surfaces define an interior volume, the upper and lower surfaces of the sac comprising porous material for allowing bone to grow into and out of the interior volume when the sac is in the expanded state, and the peripheral surface is nonporous for preventing bodily fluids from entering the sac when the sac is in the expanded state, wherein the sac is free of structural walls affixed to the peripheral surface, the sac is pre-sized and pre-shaped to fit complimentary within the implantation location, and the sac comprises a spring mechanism that permits the sac to be folded upon itself and that can be activated to expand the sac to the expanded state;

(b) a cage which is structurally configured to fit inside the sac after expansion and to maintain the sac in an expanded state after the sac has been filled with bone tissue; and (c) optionally a syringe, cannula, arthroscope, or forceps for filling the interior of the sac with bone tissue.

2. The kit according to claim 1, wherein the peripheral sides of the sac have a height which is generally equal to the desired height or distance between vertebra or bones to be fused.

3. The kit according to claim 1, wherein the sac further comprises a structural element which is opaque to medical imaging equipment.

4. The kit according to claim 3, wherein the structural element is a band or wire which encircles the peripheral surface of the sac or runs circumferentially through the sac.

5. The kit according to claim 3, wherein the structural element is pre-stressed so as to have a memory effect to facilitate placement of the sac in the body or to expand the sac into a desired position or shape.

6. The kit according to claim 1, wherein the sac comprises a radio-opaque structural element located in the equator of the sac for monitoring the placement of the sac within the body.

7. The kit according to claim 1, wherein the sac is structurally configured for filling with bone tissue without leakage of sac contents when filled.

8. The kit according to claim 1, wherein the cage is formed from a metallic, polymeric, or ceramic material, or a combination thereof.

9. The kit according to claim 1, wherein the cage has a predetermined height after expansion.

10. The kit according to claim 1, wherein the cage has an adjustable height.

11. The kit according to claim 1, wherein the cage has a collapsed state to facilitate insertion into the sac, and an expanded state which provides structural support for the sac.

12. The kit according to claim 1, wherein the cage has generally flat upper and lower surfaces in the expanded state.

13. A kit comprising:

(a) an outer sac for fusing spinal bone, the sac having a unitary structure and generally flat upper and lower surfaces and a peripheral surface between the upper and lower surfaces, the outer sac having a closed collapsible state for delivery to an implantation location, wherein the sac is folded upon itself, the outer sac having an opened expanded state when positioned at the implantation location, wherein the surfaces define an interior volume to be filled with bone tissue without leakage of sac contents when filled, the upper and lower surfaces of the outer sac comprising porous material for allowing bone to grow into and out of the interior volume when the sac is in the expanded state, and the peripheral surface is nonporous for preventing bodily fluids from entering the sac when the sac is in the expanded state, wherein the outer sac is free of structural walls affixed to the peripheral surface, and the outer sac is pre-sized and pre-shaped to fit complimentary within the implantation location, and comprises a spring mechanism that permits the outer sac to be folded upon itself and that can be activated to expand the sac to the expanded state;

(b) an inner sac which is structurally configured to fit inside the outer sac after expansion and to maintain the outer sac in an expanded state upon filling with bone tissue; and (c) optionally a syringe, cannula, arthroscope, or forceps for filling the outer sac, inner sac, or both, with bone tissue.

14. The kit according to claim 1, wherein the bone tissue comprises bone chips, bone fragments, osteocytes, bone cement, cartilage chips, cartilage-forming material, natural bone, bioengineered bone, synthetic bone, or combinations thereof.

* * * * *